(12) United States Patent
Abbate et al.

(10) Patent No.: US 7,951,185 B1
(45) Date of Patent: May 31, 2011

(54) DELIVERY OF A STENT AT AN ELEVATED TEMPERATURE

(75) Inventors: Anthony J. Abbate, Santa Clara, CA (US); Jeffrey David Royal, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1055 days.

(21) Appl. No.: 11/326,797

(22) Filed: Jan. 6, 2006

(51) Int. Cl.
*A61F 2/06* (2006.01)

(52) U.S. Cl. .................................... 623/1.11; 623/1.19

(58) Field of Classification Search ............... 623/1.1, 623/1.11, 1.19; 604/95.05, 103.01, 113, 604/96.01, 97.01; 606/192, 27–31
See application file for complete search history.

(56) References Cited

U.S. PATENT DOCUMENTS

| | | | |
|---|---|---|---|
| 2,392,199 A * | 1/1946 | Steiger | 244/98 |
| 3,687,135 A | 8/1972 | Stroganov et al. | |
| 3,839,743 A | 10/1974 | Schwarcz | |
| 3,900,632 A | 8/1975 | Robinson | |
| 4,104,410 A | 8/1978 | Malecki | |
| 4,110,497 A | 8/1978 | Hoel | |
| 4,321,711 A | 3/1982 | Mano | |
| 4,346,028 A | 8/1982 | Griffith | |
| 4,596,574 A | 6/1986 | Urist | |
| 4,599,085 A | 7/1986 | Riess et al. | |
| 4,612,009 A | 9/1986 | Drobnik et al. | |
| 4,633,873 A | 1/1987 | Dumican et al. | |
| 4,656,083 A | 4/1987 | Hoffman et al. | |
| 4,718,907 A | 1/1988 | Karwoski et al. | |
| 4,722,335 A | 2/1988 | Vilasi | |
| 4,723,549 A | 2/1988 | Wholey et al. | |
| 4,732,152 A | 3/1988 | Wallstén et al. | |
| 4,733,665 A | 3/1988 | Palmaz | |
| 4,739,762 A | 4/1988 | Palmaz | |
| 4,740,207 A | 4/1988 | Kreamer | |
| 4,743,252 A | 5/1988 | Martin, Jr. et al. | |
| 4,754,752 A * | 7/1988 | Ginsburg et al. | 606/27 |
| 4,768,507 A | 9/1988 | Fischell et al. | |
| 4,776,337 A | 10/1988 | Palmaz | |

(Continued)

FOREIGN PATENT DOCUMENTS

DE 44 07 079 9/1994

(Continued)

OTHER PUBLICATIONS

U.S. Appl. No. 10/317,435, filed Dec. 11, 2002, Hossainy et al.

(Continued)

*Primary Examiner* — Darwin P Erezo
*Assistant Examiner* — Dianne Dornbusch
(74) *Attorney, Agent, or Firm* — Squire, Sanders & Dempsey (US) LLP

(57) ABSTRACT

Methods and systems of delivering a stent at an elevated temperature are disclosed herein. Methods of delivering a stent include allowing reactants to react within a delivery system exothermically. The heat generated from the exothermic reaction increase a temperature of a stent mounted on a support member. The increase in temperature increases the flexibility of the stent which reduces or eliminates formation of cracks in the stent when it expands. A system can include a first reactant disposed within at least a portion of the support member, a catheter in fluid communication with the support member, or both. The first reactant being disposed in such a way to react exothermically with a second reactant disposed within the delivery system.

9 Claims, 3 Drawing Sheets

U.S. PATENT DOCUMENTS

| | | | |
|---|---|---|---|
| 4,799,479 A * | 1/1989 | Spears | 606/28 |
| 4,800,882 A | 1/1989 | Gianturco | |
| 4,816,339 A | 3/1989 | Tu et al. | |
| 4,818,559 A | 4/1989 | Hama et al. | |
| 4,850,999 A | 7/1989 | Planck | |
| 4,877,030 A | 10/1989 | Beck et al. | |
| 4,878,906 A | 11/1989 | Lindemann et al. | |
| 4,879,135 A | 11/1989 | Greco et al. | |
| 4,886,062 A | 12/1989 | Wiktor | |
| 4,902,289 A | 2/1990 | Yannas | |
| 4,977,901 A | 12/1990 | Ofstead | |
| 4,994,298 A | 2/1991 | Yasuda | |
| 5,019,090 A | 5/1991 | Pinchuk | |
| 5,028,597 A | 7/1991 | Kodama et al. | |
| 5,059,211 A | 10/1991 | Stack et al. | |
| 5,062,829 A | 11/1991 | Pryor et al. | |
| 5,084,065 A | 1/1992 | Weldon et al. | |
| 5,085,629 A | 2/1992 | Goldberg et al. | |
| 5,100,429 A | 3/1992 | Sinofsky et al. | |
| 5,104,410 A | 4/1992 | Chowdhary | |
| 5,108,417 A | 4/1992 | Sawyer | |
| 5,108,755 A | 4/1992 | Daniels et al. | |
| 5,112,457 A | 5/1992 | Marchant | |
| 5,123,917 A | 6/1992 | Lee | |
| 5,129,915 A * | 7/1992 | Cantenys | 606/192 |
| 5,156,623 A | 10/1992 | Hakamatsuka et al. | |
| 5,163,951 A | 11/1992 | Pinchuk et al. | |
| 5,163,952 A | 11/1992 | Froix | |
| 5,163,958 A | 11/1992 | Pinchuk | |
| 5,167,614 A | 12/1992 | Tessmann et al. | |
| 5,178,618 A * | 1/1993 | Kandarpa | 606/28 |
| 5,192,311 A | 3/1993 | King et al. | |
| 5,197,977 A | 3/1993 | Hoffman, Jr. et al. | |
| 5,234,456 A | 8/1993 | Silvestrini | |
| 5,234,457 A | 8/1993 | Andersen | |
| 5,236,447 A | 8/1993 | Kubo et al. | |
| 5,279,594 A | 1/1994 | Jackson | |
| 5,282,860 A | 2/1994 | Matsuno et al. | |
| 5,289,831 A | 3/1994 | Bosley | |
| 5,290,271 A | 3/1994 | Jernberg | |
| 5,306,286 A | 4/1994 | Stack et al. | |
| 5,306,294 A | 4/1994 | Winston et al. | |
| 5,328,471 A | 7/1994 | Slepian | |
| 5,330,500 A | 7/1994 | Song | |
| 5,342,348 A | 8/1994 | Kaplan | |
| 5,342,395 A | 8/1994 | Jarrett et al. | |
| 5,342,621 A | 8/1994 | Eury | |
| 5,356,433 A | 10/1994 | Rowland et al. | |
| 5,383,925 A | 1/1995 | Schmitt | |
| 5,385,580 A | 1/1995 | Schmitt | |
| 5,389,106 A | 2/1995 | Tower | |
| 5,399,666 A | 3/1995 | Ford | |
| 5,423,885 A | 6/1995 | Williams | |
| 5,441,515 A | 8/1995 | Khosravi et al. | |
| 5,443,458 A | 8/1995 | Eury | |
| 5,443,500 A | 8/1995 | Sigwart | |
| 5,455,040 A | 10/1995 | Marchant | |
| 5,464,650 A | 11/1995 | Berg et al. | |
| 5,502,158 A | 3/1996 | Sinclair et al. | |
| 5,514,379 A | 5/1996 | Weissleder et al. | |
| 5,527,337 A | 6/1996 | Stack et al. | |
| 5,545,408 A | 8/1996 | Trigg et al. | |
| 5,554,120 A | 9/1996 | Chen et al. | |
| 5,556,413 A | 9/1996 | Lam | |
| 5,578,046 A | 11/1996 | Liu et al. | |
| 5,578,073 A | 11/1996 | Haimovich et al. | |
| 5,591,199 A | 1/1997 | Porter et al. | |
| 5,591,607 A | 1/1997 | Gryaznov et al. | |
| 5,593,403 A | 1/1997 | Buscemi | |
| 5,593,434 A | 1/1997 | Williams | |
| 5,599,301 A | 2/1997 | Jacobs et al. | |
| 5,599,922 A | 2/1997 | Gryaznov et al. | |
| 5,605,696 A | 2/1997 | Eury et al. | |
| 5,607,442 A | 3/1997 | Fischell et al. | |
| 5,607,467 A | 3/1997 | Froix | |
| 5,618,299 A | 4/1997 | Khosravi et al. | |
| 5,629,077 A | 5/1997 | Turnlund et al. | |
| 5,631,135 A | 5/1997 | Gryaznov et al. | |
| 5,632,771 A | 5/1997 | Boatman et al. | |
| 5,632,840 A | 5/1997 | Campbell | |
| 5,637,113 A | 6/1997 | Tartaglia et al. | |
| 5,649,977 A | 7/1997 | Campbell | |
| 5,667,767 A | 9/1997 | Greff et al. | |
| 5,667,796 A | 9/1997 | Otten | |
| 5,670,161 A | 9/1997 | Healy et al. | |
| 5,670,558 A | 9/1997 | Onishi et al. | |
| 5,693,085 A | 12/1997 | Buirge et al. | |
| 5,700,286 A | 12/1997 | Tartaglia et al. | |
| 5,707,385 A | 1/1998 | Williams | |
| 5,711,763 A | 1/1998 | Nonami et al. | |
| 5,716,981 A | 2/1998 | Hunter et al. | |
| 5,725,549 A | 3/1998 | Lam | |
| 5,726,297 A | 3/1998 | Gryaznov et al. | |
| 5,728,751 A | 3/1998 | Patnaik | |
| 5,733,326 A | 3/1998 | Tomonto et al. | |
| 5,733,330 A | 3/1998 | Cox | |
| 5,733,564 A | 3/1998 | Lehtinen | |
| 5,733,925 A | 3/1998 | Kunz et al. | |
| 5,741,881 A | 4/1998 | Patnaik | |
| 5,756,457 A | 5/1998 | Wang et al. | |
| 5,756,476 A | 5/1998 | Epstein et al. | |
| 5,765,682 A | 6/1998 | Bley et al. | |
| 5,766,204 A | 6/1998 | Porter et al. | |
| 5,766,239 A | 6/1998 | Cox | |
| 5,766,710 A | 6/1998 | Turnlund et al. | |
| 5,769,883 A | 6/1998 | Buscemi et al. | |
| 5,780,807 A | 7/1998 | Saunders | |
| 5,800,516 A | 9/1998 | Fine et al. | |
| 5,811,447 A | 9/1998 | Kunz et al. | |
| 5,824,049 A | 10/1998 | Ragheb et al. | |
| 5,830,178 A | 11/1998 | Jones et al. | |
| 5,830,461 A | 11/1998 | Billiar et al. | |
| 5,830,879 A | 11/1998 | Isner | |
| 5,833,651 A | 11/1998 | Donovan et al. | |
| 5,834,582 A | 11/1998 | Sinclair et al. | |
| 5,836,962 A | 11/1998 | Gianotti | |
| 5,837,313 A | 11/1998 | Ding et al. | |
| 5,837,835 A | 11/1998 | Gryaznov et al. | |
| 5,840,083 A | 11/1998 | Braach-Maksvytis | |
| 5,851,508 A | 12/1998 | Greff et al. | |
| 5,853,408 A * | 12/1998 | Muni | 606/27 |
| 5,854,207 A | 12/1998 | Lee et al. | |
| 5,855,612 A | 1/1999 | Ohthuki et al. | |
| 5,855,618 A | 1/1999 | Patnaik et al. | |
| 5,858,746 A | 1/1999 | Hubbell et al. | |
| 5,865,814 A | 2/1999 | Tuch | |
| 5,868,781 A | 2/1999 | Killion | |
| 5,873,904 A | 2/1999 | Ragheb et al. | |
| 5,874,101 A | 2/1999 | Zhong et al. | |
| 5,874,109 A | 2/1999 | Ducheyne et al. | |
| 5,874,165 A | 2/1999 | Drumheller | |
| 5,876,743 A | 3/1999 | Ibsen et al. | |
| 5,877,263 A | 3/1999 | Patnaik et al. | |
| 5,879,713 A | 3/1999 | Roth et al. | |
| 5,888,533 A | 3/1999 | Dunn | |
| 5,891,192 A | 4/1999 | Murayama et al. | |
| 5,897,955 A | 4/1999 | Drumheller | |
| 5,906,759 A | 5/1999 | Richter | |
| 5,914,182 A | 6/1999 | Drumheller | |
| 5,916,870 A | 6/1999 | Lee et al. | |
| 5,922,005 A | 7/1999 | Richter et al. | |
| 5,942,209 A | 8/1999 | Leavitt et al. | |
| 5,948,428 A | 9/1999 | Lee et al. | |
| 5,954,744 A | 9/1999 | Phan et al. | |
| 5,957,962 A * | 9/1999 | Wallsten et al. | 607/104 |
| 5,957,975 A | 9/1999 | Lafont et al. | |
| 5,965,720 A | 10/1999 | Gryaznov et al. | |
| 5,971,954 A | 10/1999 | Conway et al. | |
| 5,976,182 A | 11/1999 | Cox | |
| 5,980,564 A | 11/1999 | Stinson | |
| 5,980,928 A | 11/1999 | Terry | |
| 5,980,972 A | 11/1999 | Ding | |
| 5,981,568 A | 11/1999 | Kunz et al. | |
| 5,986,169 A | 11/1999 | Gjunter | |
| 5,992,419 A * | 11/1999 | Sterzer et al. | 128/898 |
| 5,997,468 A | 12/1999 | Wolff et al. | |
| 6,010,445 A | 1/2000 | Armini et al. | |

| Patent No. | Date | Name |
|---|---|---|
| 6,015,541 A | 1/2000 | Greff et al. |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,066,156 A | 5/2000 | Yan |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,083,258 A | 7/2000 | Yadav |
| 6,093,463 A | 7/2000 | Thakrar |
| 6,096,070 A | 8/2000 | Ragheb et al. |
| 6,096,525 A | 8/2000 | Patnaik |
| 6,099,562 A | 8/2000 | Ding et al. |
| 6,103,230 A | 8/2000 | Billiar et al. |
| 6,107,416 A | 8/2000 | Patnaik et al. |
| 6,110,188 A | 8/2000 | Narciso, Jr. |
| 6,113,629 A | 9/2000 | Ken |
| 6,117,979 A | 9/2000 | Hendriks et al. |
| 6,120,536 A | 9/2000 | Ding et al. |
| 6,120,904 A | 9/2000 | Hostettler et al. |
| 6,121,027 A | 9/2000 | Clapper et al. |
| 6,125,523 A | 10/2000 | Brown et al. |
| 6,127,173 A | 10/2000 | Eckstein et al. |
| 6,129,761 A | 10/2000 | Hubbell |
| 6,129,928 A | 10/2000 | Sarangapani et al. |
| 6,150,630 A | 11/2000 | Perry et al. |
| 6,153,252 A | 11/2000 | Hossainy et al. |
| 4,776,337 A | 12/2000 | Palmaz |
| 6,159,951 A | 12/2000 | Karpeisky et al. |
| 6,160,084 A | 12/2000 | Langer et al. |
| 6,165,212 A | 12/2000 | Dereume et al. |
| 6,166,130 A | 12/2000 | Rhee et al. |
| 6,169,170 B1 | 1/2001 | Gryaznov et al. |
| 6,171,609 B1 | 1/2001 | Kunz |
| 6,174,330 B1 | 1/2001 | Stinson |
| 6,177,523 B1 | 1/2001 | Reich et al. |
| 6,183,505 B1 | 2/2001 | Mohn, Jr. et al. |
| 6,187,045 B1 | 2/2001 | Fehring et al. |
| 6,210,715 B1 | 4/2001 | Starling et al. |
| 6,224,626 B1 | 5/2001 | Steinke |
| 6,228,845 B1 | 5/2001 | Donovan et al. |
| 6,240,616 B1 | 6/2001 | Yan |
| 6,245,076 B1 | 6/2001 | Yan |
| 6,245,103 B1 | 6/2001 | Stinson |
| 6,248,344 B1 | 6/2001 | Ylanen et al. |
| 6,251,135 B1 | 6/2001 | Stinson et al. |
| 6,251,142 B1 | 6/2001 | Bernacca et al. |
| 6,273,913 B1 | 8/2001 | Wright et al. |
| 6,281,262 B1 | 8/2001 | Shikinami |
| 6,284,333 B1 | 9/2001 | Wang et al. |
| 6,287,332 B1 | 9/2001 | Bolz et al. |
| 6,290,721 B1 | 9/2001 | Heath |
| 6,293,966 B1 | 9/2001 | Frantzen |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 4,733,665 C2 | 1/2002 | Palmaz |
| 6,375,826 B1 | 4/2002 | Wang et al. |
| 6,379,381 B1 | 4/2002 | Hossainy et al. |
| 6,387,121 B1 | 5/2002 | Alt |
| 6,388,043 B1 | 5/2002 | Langer et al. |
| 6,395,326 B1 | 5/2002 | Castro et al. |
| 6,409,761 B1 | 6/2002 | Jang |
| 6,423,092 B2 | 7/2002 | Datta et al. |
| 6,461,632 B1 | 10/2002 | Gogolewski |
| 6,464,720 B2 | 10/2002 | Boatman et al. |
| 6,479,565 B1 | 11/2002 | Stanley |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Wenz et al. |
| 6,511,748 B1 | 1/2003 | Barrows |
| 6,517,888 B1 | 2/2003 | Weber |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |
| 6,554,854 B1 | 4/2003 | Flanagan |
| 6,565,599 B1 | 5/2003 | Hong et al. |
| 6,569,191 B1 | 5/2003 | Hogan |
| 6,569,193 B1 | 5/2003 | Cox et al. |
| 6,572,672 B2 | 6/2003 | Yadav et al. |
| 6,574,851 B1 | 6/2003 | Mirizzi |
| 6,585,755 B2 | 7/2003 | Jackson et al. |
| 6,592,614 B2 | 7/2003 | Lenker et al. |
| 6,592,617 B2 | 7/2003 | Thompson |
| 6,613,072 B2 | 9/2003 | Lau et al. |
| 6,613,082 B2 * | 9/2003 | Yang ............................ 623/1.42 |
| 6,626,939 B1 | 9/2003 | Burnside et al. |
| 6,635,269 B1 | 10/2003 | Jennissen |
| 6,645,243 B2 | 11/2003 | Vallana et al. |
| 6,656,162 B2 | 12/2003 | Santini, Jr. et al. |
| 6,664,335 B2 | 12/2003 | Krishnan |
| 6,666,214 B2 | 12/2003 | Canham |
| 6,667,049 B2 | 12/2003 | Janas et al. |
| 6,669,723 B2 | 12/2003 | Killion et al. |
| 6,676,697 B1 | 1/2004 | Richter |
| 6,679,980 B1 | 1/2004 | Andreacchi |
| 6,682,553 B1 * | 1/2004 | Webler, Jr. .................... 623/1.11 |
| 6,689,375 B1 | 2/2004 | Wahlig et al. |
| 6,695,920 B1 | 2/2004 | Pacetti et al. |
| 6,706,273 B1 | 3/2004 | Roessler |
| 6,709,379 B1 | 3/2004 | Brandau et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,746,773 B2 | 6/2004 | Llanos et al. |
| 6,752,826 B2 | 6/2004 | Holloway et al. |
| 6,753,007 B2 | 6/2004 | Haggard et al. |
| 6,764,505 B1 | 7/2004 | Hossainy et al. |
| 6,818,063 B1 | 11/2004 | Kerrigan |
| 6,846,323 B2 | 1/2005 | Yip et al. |
| 7,008,446 B1 * | 3/2006 | Amis et al. .................... 623/1.21 |
| 7,220,394 B2 * | 5/2007 | Sreeram et al. ................. 423/53 |
| 7,316,711 B2 * | 1/2008 | Allen et al. .................... 623/1.15 |
| 7,662,082 B2 * | 2/2010 | White et al. ...................... 600/3 |
| 7,763,065 B2 * | 7/2010 | Schmid et al. ................ 623/1.15 |
| 7,794,494 B2 * | 9/2010 | Sahatjian et al. ............. 623/1.42 |
| 2001/0044652 A1 | 11/2001 | Moore |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0062148 A1 | 5/2002 | Hart |
| 2002/0065553 A1 | 5/2002 | Weber |
| 2002/0111590 A1 | 8/2002 | Davila et al. |
| 2002/0116050 A1 | 8/2002 | Kocur |
| 2002/0138133 A1 | 9/2002 | Lenz et al. |
| 2002/0161114 A1 | 10/2002 | Gunatillake et al. |
| 2003/0033001 A1 | 2/2003 | Igaki |
| 2003/0093107 A1 | 5/2003 | Parsonage et al. |
| 2003/0100865 A1 | 5/2003 | Santini, Jr. et al. |
| 2003/0105518 A1 | 6/2003 | Dutta |
| 2003/0105530 A1 | 6/2003 | Pirhonen |
| 2003/0163190 A1 * | 8/2003 | LaFont et al. ................ 623/1.11 |
| 2003/0171053 A1 | 9/2003 | Sanders |
| 2003/0187495 A1 | 10/2003 | Cully et al. |
| 2003/0208259 A1 | 11/2003 | Penhasi |
| 2003/0209835 A1 | 11/2003 | Chun et al. |
| 2003/0226833 A1 | 12/2003 | Shapovalov et al. |
| 2003/0236563 A1 | 12/2003 | Fifer |
| 2004/0093077 A1 | 5/2004 | White et al. |
| 2004/0098095 A1 | 5/2004 | Burnside et al. |
| 2004/0111149 A1 | 6/2004 | Stinson |
| 2004/0127970 A1 | 7/2004 | Saunders et al. |
| 2004/0143317 A1 | 7/2004 | Stinson et al. |
| 2004/0148014 A1 * | 7/2004 | Nuutinen et al. ............. 623/1.15 |
| 2004/0167600 A1 * | 8/2004 | LaFont et al. ................ 623/1.11 |
| 2004/0167610 A1 | 8/2004 | Fleming, III |
| 2004/0193179 A1 * | 9/2004 | Nikolchev .................... 606/108 |
| 2004/0267350 A1 | 12/2004 | Roubin et al. ................. 623/1.13 |
| 2005/0010275 A1 * | 1/2005 | Sahatjian et al. ............. 623/1.11 |
| 2005/0049666 A1 * | 3/2005 | Chien et al. .................. 623/1.11 |

FOREIGN PATENT DOCUMENTS

| | | |
|---|---|---|
| DE | 197 31 021 | 1/1999 |
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |
| GB | 2 247 696 | 3/1992 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 2004/023985 | 3/2004 |

OTHER PUBLICATIONS

Anonymous, *Bioabsorbable stent mounted on a catheter having optical coherence tomography capabilities*, Research Disclosure, Sep. 2004, pp. 1159-1162.

Ansari, *End-to-end tubal anastomosis using an absorbable stent*, Fertility and Sterility, vol. 32(2), pp. 197-201 (Aug. 1979).

Ansari, *Tubal Reanastomosis Using Absorbable Stent*, International Journal of Fertility, vol. 23(4), pp. 242-243 (1978).

Bull, *Parylene Coating for Medical Applications*, Medical Product Manufacturing News 18, 1 pg. (Mar. 1993).

Casper et al., *Fiber-Reinforced Absorbable Composite for Orthopedic Surgery*, Polymeric Materials Science and Engineering, vol. 53 pp. 497-501 (1985).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Devanathan et al., *Polymeric Conformal Coatings for Implantable Electronic Devices*, IEEE Transactions in Biomedical Engineering, vol. BME-27(11), pp. 671-675 (1980).

Elbert et al., *Conjugate Addition Reactions Combined with Free-Radical Cross-Linking for the Design of Materials for Tissue Engineering*, Biomacromolecules, vol. 2, pp. 430-441 (2001).

Hahn et al., *Biocompatibility of Glow-Discharge-Polymerized Films and Vacuum-Deposited Parylene*, J Applied Polymer Sci, vol. 38, pp. 55-64 (1984).

Hahn et al., *Glow Discharge Polymers as Coatings for Implanted Devices*, ISA, pp. 109-111 (1981).

He et al., *Assessment of Tissue Blood Flow Following Small Artery Welding with an Intraluminal Dissolvable Stent*, Microsurgery, vol. 19(3), pp. 148-152 (1999).

Kelley et al., *Totally Resorbable High-Strength Composite Material*, Advances in Biomedical Polymers, vol. 35, pp. 75-85 (1987).

Kubies et al., *Microdomain Structure in polylactide-block-poly(ethylene oxide) copolymer films*, Biomaterials, vol. 21, pp. 529-536 (2000).

Kutryk et al., *Coronary Stenting: Current Perspectives*, a companion to the Handbook of Coronary Stents, p. 1-16 (1999).

Martin et al., *Enhancing the biological activity of immobilized osteopontin using a type-1 collagen affinity coating*, J. Biomed. Mater. Res., vol. 70A, pp. 10-19 (2004).

Mauduit et al., *Hydrolytic degradation of films prepared from blends of high and low molecular weight poly(DL-lactic acid)s*, J. Biomed. Mater. Res., vol. 30, pp. 201-207 (1996).

Middleton et al., *Synthetic biodegradable polymers as orthopedic devices*, Biomaterials, vol. 21, pp. 2335-2346 (2000).

Muller et al., *Advances in Coronary Angioplasty: Endovascular Stents*, Coron. Arter. Dis., vol. 1(4), pp. 438-448 (Jul./Aug. 1990).

Nichols et al., *Electrical Insulation of Implantable Devices by Composite Polymer Coatings*, ISA Transactions, vol. 26(4), pp. 15-18 1987.

Peuster et al., *A novel approach to temporary stenting: degradable cardiovascular stents produced from corrodible metal-results 6-18 months after implantation into New Zealand white rabbits*, Heart, vol. 86, pp. 563-569 (2001).

Pietrzak et al., *Bioabsorbable Fixation Devices: Status for the Craniomaxillofacial Surgeon*, J. Craniofaxial Surg., vol. 2, pp. 92-96 (1997).

Pietrzak et al., *Bioresorbable implants—practical considerations*, Bone, vol. 19, No. 1, Supplement Jul. 1996, pp. 109S-119S.

Redman, *Clinical Experience with Vasovasostomy Utilizing Absorbable Intravasal Stent*, Urology, vol. 20(1), pp. 59-61 (Jul. 1982).

Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, vol. 79(2), pp. 445-457 (Feb. 1989).

Schmidt et al., *Long-Term Implants of Parylene-C Coated Microelectrodes*, Med & Biol Eng & Comp, vol. 26(1), pp. 96-101 (Jan. 1988).

Spagnuolo et al., *Gas 1 is induced by VE-cadherin and vascular endothelial growth factor and inhibits endothelial cell apoptosis*, Blood, vol. 103, pp. 3005-3012 (2004).

Tamai et al., *Initial and 6-Month Results of Biodegradable Poly-I-Lactic Acid Coronary Stents in Humans*, Circulation, pp. 399-404 (Jul. 25, 2000).

Tsuji et al., *Biodegradable Polymeric Stents*, Current Interventional Cardiology Reports, vol. 3, pp. 10-17 (2001).

Völkel et al., *Targeting of immunoliposomes to endothelial cells using a single—chain Fv fragment directed against human endoglin (CD105)*, Biochimica et Biophysica Acta 1663, pp. 158-166 (2004).

von Recum et al., *Degradation of polydispersed poly(L-lactic acid) to modulate lactic acid release*, Biomaterials, vol. 16, pp. 441-445 (1995).

Yau et al., Modern Size-Exclusion Liquid Chromatography, Wiley-Interscience Publication, IX-XV (1979).

* cited by examiner

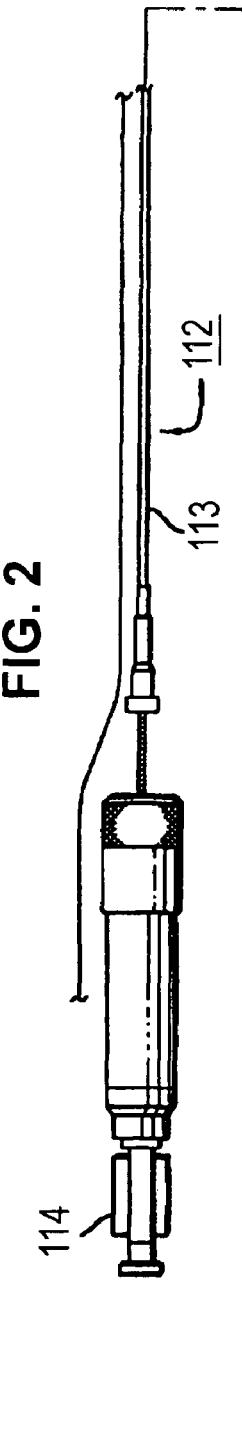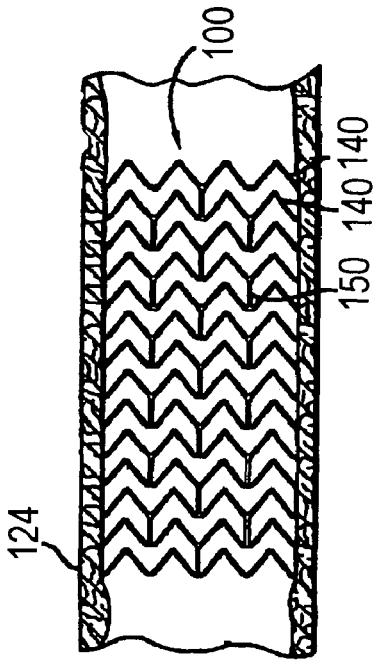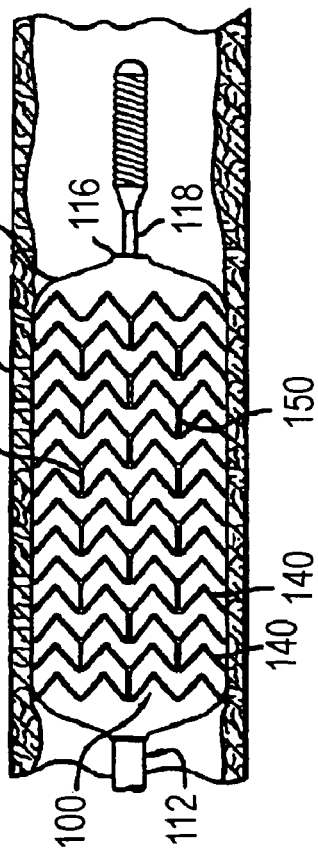

DELIVERY OF A STENT AT AN ELEVATED TEMPERATURE

BACKGROUND OF THE INVENTION

1. Field of the Invention

This invention relates to methods and systems for delivery of polymeric stents.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil. In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodible materials such as bioabsorbable polymers should be configured to completely erode only after the clinical need for them has ended.

A potential problem with polymeric stents is that their struts or bar arms can crack during crimping and expansion. This is especially the case with brittle polymers. The localized portions of the stent pattern subjected to substantial deformation during crimping and expansion tend to be the most vulnerable to failure.

Another potential problem with polymeric stents is creep. Creep is a consequence of the viscoelastic nature of polymeric materials. Creep refers to the gradual deformation that occurs in a polymeric material subjected to an applied load. Creep occurs even when the applied load is constant. Creep in a polymeric stent reduces the effectiveness of a stent in maintaining a desired vascular patency. In particular, creep allows inward radial forces to permanently deform a stent radially inward.

Therefore, it is desirable for a stent to have flexibility and resistance to cracking during deployment. It is also advantageous for a stent to be rigid and resistant to creep after deployment.

SUMMARY OF THE INVENTION

Certain embodiments of the present invention are directed to a method of delivering a stent mounted on a support member of a delivery system. The method may include allowing a first reactant and a second reactant to react within the delivery system, wherein the first and the second reactants react exothermically. The method may further include allowing heat generated from the exothermic reaction to increase a temperature of the stent mounted on the support member. The increase in temperature may increase the flexibility of the stent such that formation of cracks in the stent upon its expansion is reduced or eliminated.

Further embodiments of the present invention are directed to a delivery system for delivering a stent at an implant site in a bodily lumen including a support member for supporting the stent. The support member may be coupled to a catheter in fluid communication with the support member. A first reactant may be disposed within at least a portion of the support member, catheter, or both. The first reactant may be disposed in such a way to react exothermically with a second reactant disposed within the delivery system. The heat generated from the exothermic reaction may increase a temperature of the stent mounted on the support member. The increase in temperature may increase the flexibility of the stent such that formation of cracks in the stent upon its expansion is reduced or eliminated.

BRIEF DESCRIPTION OF THE DRAWINGS

FIG. 2 depicts an elevation view, partially in section, of a stent mounted on a delivery system.

FIG. 3 depicts an elevation view, partially in section, with a stent expanded within an artery.

FIG. 4 depicts an elevation view, partially in section, showing an expanded stent after withdrawal of a delivery catheter.

DETAILED DESCRIPTION OF THE INVENTION

Figure 1:
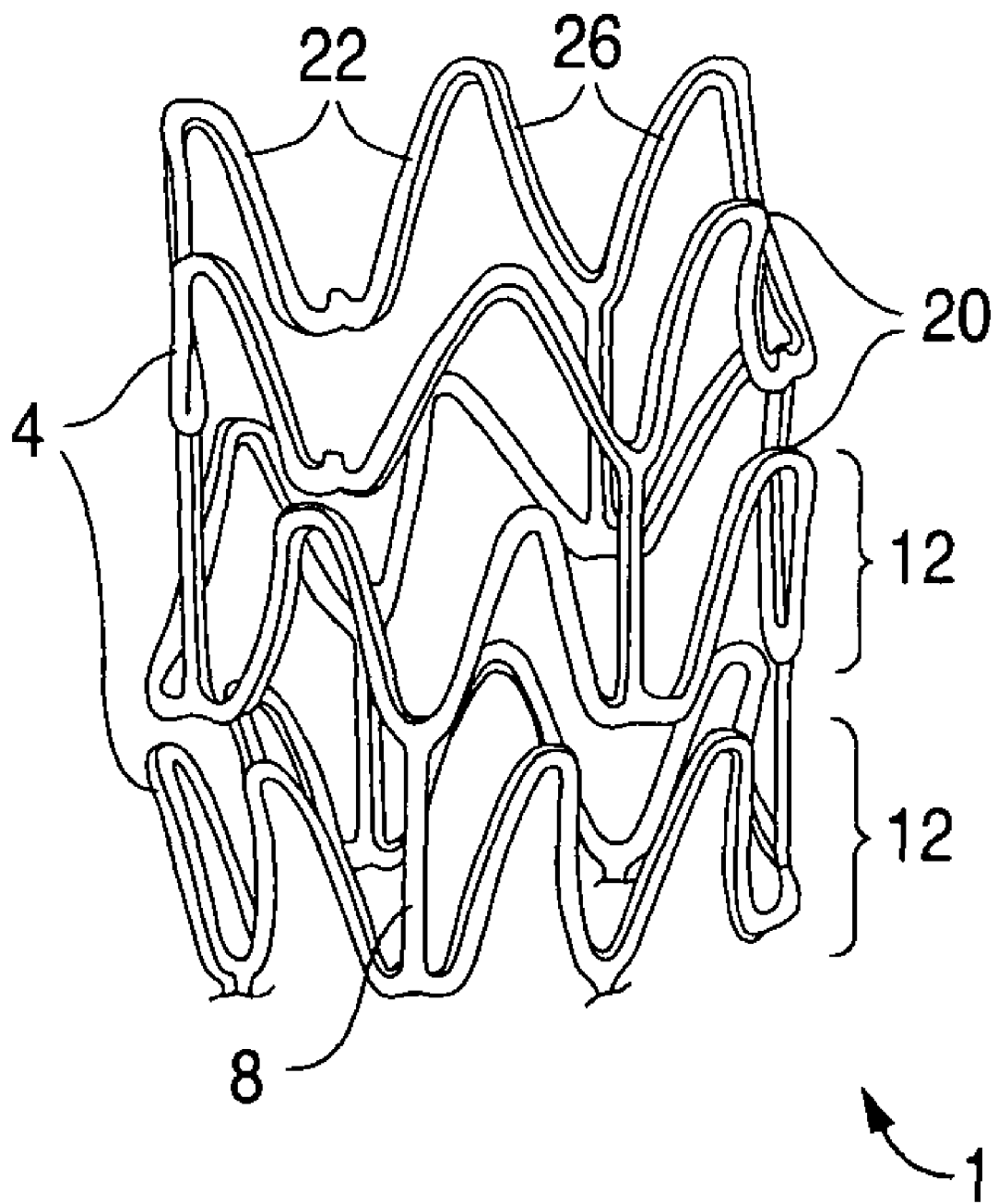
FIG. 1 depicts a stent.

Various embodiments of a method and system for delivery of stents are provided herein. In general, the embodiments relate to delivery of a stent at an elevated temperature. The elevated temperature increases the flexibility of the stent such that formation of cracks in the stent upon its expansion is reduced or eliminated. These embodiments may be applied in the delivery of balloon expandable and self-expandable stents. Embodiments of the method and system may also be applied to other implantable medical devices including, but not limited to, stent-grafts and grafts (e.g., aortic grafts).

Many treatment applications only require the presence of a stent in a bodily lumen for a limited period of time. To accommodate this, a stent can be made of a biodegradable polymer. A stent can also be made of a biostable or a combination of a biostable and biodegradable polymer. A stent made from a biodegradable polymer is intended to remain in the body for a duration of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain. In some embodiments, very negligible traces or residue may be left behind.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

The underlying structure or substrate of an implantable medical device, such as a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

Representative examples of polymers that may be used to fabricate or coat an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating an implantable medical device include ethylene vinyl alcohol copolymer (commonly known by the generic name EVOH or by the trade name EVAL), poly(butyl methacrylate), poly (vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

Implantable medical devices are typically subjected to stress during use, both before and during treatment. "Use" includes, but is not limited to, manufacturing, assembling (e.g., crimping stent on a catheter), delivery of a stent into and through a bodily lumen to a treatment site, and deployment of a stent at a treatment site. Both a scaffolding and a coating on a scaffolding experience stress that result in strain in the scaffolding and/or coating. For example, during deployment, the scaffolding of a stent can be exposed to stress caused by the radial expansion of the stent body. In addition, the scaffolding and/or coating may be exposed to stress when it is mounted on a catheter from crimping or compression of the stent.

Implantable medical devices, such as stents, that relate to the embodiments described herein typically include an underlying scaffolding or substrate. The underlying structure or substrate of the device can be of virtually any design. The substrate may have a polymer-based coating that may contain, for example, an active agent or drug for local administration at a diseased site. The active agent can be any substance capable of exerting a therapeutic or prophylactic effect.

FIG. 1 depicts a three-dimensional view of an exemplary embodiment of a cylindrically-shaped stent 1 with struts 4 that form cylindrical rings 12 which are connected by linking struts 8. The cross-section of the struts in stent 1 is rectangular-shaped. The struts have abluminal faces 20, luminal faces 22, and sidewall faces 26. The cross-section of struts is not limited to what has been illustrated, and therefore, other cross-sectional shapes are applicable with embodiments of the present invention. The pattern should not be limited to what has been illustrated as other stent patterns are easily applicable with embodiments of the present invention.

In general, a stent pattern is designed so that the stent can be radially compressed (crimped) and radially expanded (to allow deployment). The stresses involved during compression and expansion are generally distributed throughout various structural elements of the stent pattern. As a stent expands, various portions of the stent can deform to accomplish a radial expansion.

Additionally, fabrication of an implantable medical device, such as a stent, may include forming a pattern that includes a plurality of interconnecting structural elements or struts on a tube. Polymer tubes may be formed by various methods, including, but not limited to extrusion or injection molding. In some embodiments, the diameter of the polymer tube prior to fabrication of an implantable medical device may be between about 0.2 mm and about 5.0 mm, or more narrowly between about 1 mm and about 3 mm. In some embodiments, forming a pattern on a tube may include laser cutting a pattern on the tube. Representative examples of lasers that may be used include, but are not limited to, excimer, carbon dioxide, and YAG. In other embodiments, chemical etching may be used to form a pattern on a tube.

FIGS. 2-4 illustrate an exemplary delivery system for delivering a balloon expandable stent. FIG. 2 depicts a stent 100 with interconnected cylindrical rings 140 mounted on a catheter assembly 112 which is used to deliver stent 100 and implant it in a bodily lumen. Rings 140 are connected by links 150.

For example, a bodily lumen may include a coronary artery, peripheral artery, or other vessel or lumen within the body. The catheter assembly includes a catheter shaft 113 which has a proximal end 114 and a distal end 116. The catheter assembly is configured to advance through a vascular system over a guide wire by any of the well-known methods of an over-the-wire system (not shown) or a well-known rapid exchange catheter system, such as the one shown in FIG. 2. Stent 100 in FIGS. 2-4 conceptually represents any type of stent well-known in the art, i.e., one having a plurality of rings 140.

Catheter assembly 112, as depicted in FIG. 2, includes a port 120 where guide wire 118 exits the catheter. The distal end of guide wire 118 exits catheter distal end 116 so that the catheter advances along the guide wire on a section of the catheter between port 120 and catheter distal end 116. As is known in the art, the guide wire lumen which receives the guide wire is sized for receiving various diameter guide wires to suit a particular application. The stent is mounted on an expandable member 122 (e.g., a balloon) and is crimped tightly thereon, so that the stent and expandable member present a low profile diameter for delivery through the arteries.

As shown in FIG. 2, a partial cross-section of an artery 124 has a small amount of plaque that has been previously treated by angioplasty or other repair procedure. Stent 100 can be used to repair a diseased or damaged arterial wall as shown in FIG. 2, or a dissection, or a flap, all of which are commonly found in the coronary arteries and other vessels. Stent 100, and other embodiments of stents, also can be placed and implanted without any prior angioplasty.

In a typical procedure to implant stent 100, guide wire 118 is advanced through the vascular system by well-known methods, so that the distal end of the guide wire is advanced past the plaque or a diseased area 126. Prior to implanting the stent, the cardiologist may wish to perform an angioplasty or other procedure (i.e., atherectomy) in order to open and remodel the vessel and the diseased area. Thereafter, stent delivery catheter assembly 112 is advanced over the guide wire so that the stent is positioned in the implant area or site.

The expandable member or balloon 122 is inflated by injecting a fluid into proximal end 114 of the catheter. Balloon 122 expands radially outwardly and in turn expands the stent radially outwardly until the stent is apposed to the vessel wall. Expandable member 122 is then deflated and the catheter withdrawn from the patient's vascular system.

The guide wire typically is left in the lumen for post-dilatation procedures, if any, and subsequently is withdrawn from the vascular system. As depicted in FIGS. 3 and 4, the balloon is fully inflated with the stent expanded and pressed against the vessel wall. In FIG. 4, the implanted stent remains in the vessel after the balloon has been deflated and the catheter assembly and guide wire have been withdrawn from the patient. Stent 100 holds open the artery after the catheter is withdrawn, as illustrated by FIG. 4.

In the case of a self-expandable stent, constraining members such as sheaths may be used to secure a self-expanding stent to a catheter. The stent, constrained or secured by the sheath, is positioned at a desired treatment location. The sheath is then withdrawn which allows the stent to self-expand. Expansion is typically spontaneous. Additionally, a sheath may also be used when delivering a balloon-expandable stent. In this case, a sheath inhibits or prevents detachment of the crimped stent from the catheter prior to deployment of the crimped stent at an implant site.

As indicated above, the structural members of polymeric stents can crack during crimping and radial expansion. This can lead to mechanical failure of stent after deployment. Such cracking or rupturing can cause a stent strut to dislodge. The dislodged stent can cause an embolism in the lumen of the tubular organ. In addition, a dislodged stent can orient itself perpendicular to blood flow thereby causing thrombosis.

Rigid polymers are particularly susceptible to cracking when deformed such as when a stent is radially expanded. Polymers below their glass transition temperature tend to be rigid. The "glass transition temperature," $T_g$, is the temperature at which the amorphous domains of a polymer change from a brittle vitreous state to a solid deformable or ductile state at atmospheric pressure. In other words, the $T_g$ corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. $T_g$ of a given polymer can be dependent on the heating rate and can be influenced by the thermal history of the polymer. Furthermore, the chemical structure of the polymer heavily influences the glass transition by affecting mobility.

Below the $T_g$ of a polymer, polymer segments may not have sufficient energy to move past one another. A polymer in a rigid state may be better suited to resist radial compressive forces in a stent once a stent is deployed. Thus, it would be advantageous for the polymer of a stent to have a $T_g$ that is above body temperature. However, such a polymer when it is below its $T_g$ is susceptible to embrittlement and cracking during radial expansion.

As the temperature of a polymer is increased close to or above $T_g$, the energy barriers to rotation decrease and segmental mobility of polymer chains tends to increase. Consequently, polymers become more flexible, and thus, more resistant to embrittlement and cracking when they are at a temperature that is close to or above $T_g$. Therefore, it may be more desirable for a polymeric stent to be close to or above the $T_g$ of the polymer when a stent is expanded.

However, polymers tend to be more susceptible to creep when they are close to or above the $T_g$. Additionally, creep can also result in a polymeric stent under stress. In particular, creep allows inward radial forces to permanently deform a stent radially inward. Therefore, creep reduces the effectiveness of a stent in maintaining a desired vascular patency.

In general, it is desirable to have a delivery system that allows a stent to be (1) flexible and resistant to cracking during expansion (2) rigid and resistant to compressive forces so as to maintain vascular patency after deployment at an implant site.

Various embodiments of a method and system for delivering a stent in a bodily lumen that meet these criteria are disclosed. In general, the criteria may be met in part by using a stent fabricated from a polymer that is rigid at body temperature, e.g., a polymer with a $T_g$ greater than body temperature. The other criterion may be met by increasing the flexibility of the stent during expansion such that formation of cracks in the stent upon its expansion is reduced or eliminated. This may be accomplished by heating a stent to a temperature close to, at, or above its $T_g$.

In certain embodiments, a delivery system for delivering a stent at an implant site in a bodily lumen may include a support member for supporting the stent and a catheter in fluid communication with the support member. The support member may be an expandable member such as a catheter balloon, as described above. Alternatively, in the case of a self-expanding stent, the supporting member may be a portion of a catheter.

In certain embodiments, a method of delivering a stent mounted on a support member of the delivery system may include allowing a first reactant and a second reactant to react within the delivery system. The method may include disposing the first reactant and the second reactant within a portion of the delivery system to react. In one embodiment, the first reactant and the second reactant may be combined in a fluid to allow the reaction followed by disposing the fluid into the delivery system.

In an embodiment, the first and second reactants may react in a fluid within the support member, a catheter in fluid communication with the support member, or both. The first and the second reactants may react exothermically. The method may further include allowing heat generated from the exothermic reaction to increase a temperature of the stent mounted on the support member. The method may also include allowing the stent to cool after the stent is expanded and the reaction no longer heats the stent.

Moreover, the reaction may include one or more additional reactants. In an embodiment, the additional reactants may be disposed in the delivery system to allow the reaction to occur. In addition, the reaction may be facilitated by the presence of a catalyst. A "catalyst" refers to a substance that increases the rate of a chemical reaction by reducing the activation energy, but which is left unchanged by the reaction. The method may include disposing the catalyst in the delivery system.

Representative reactants that may be used include, but are not limited to water ($H_2O$) and sodium peroxide ($Na_2O_2$); glycerin and potassium nitrate ($KNO_3$); and sulfur and sugar.

In an embodiment, the increase in temperature may increase the flexibility of the stent such that formation of cracks in the stent upon its expansion is reduced or eliminated. The heat from the reaction may increase a temperature of the stent close to, at, or above a glass transition temperature of the polymer of the stent.

As indicated above, the support member may be an expandable member for expanding a balloon-expandable stent. Thus, one embodiment of the method may further include expanding the stent by inflating the expandable member. After expansion of the stent, the balloon may be deflated and removed from the implant site. In some embodiments, the stent may be allowed to heat set for a period of time by keeping the balloon inflated. "Heat setting" refers to the equilibration of polymer chains at an elevated temperature. In the case of a self-expandable stent, another embodiment of the method may further include allowing the stent to self-expand.

Additionally, reactants may be disposed in a solid or fluid phase. One or more of the reactants may be a liquid or dissolved in a solvent. Fluids may be injected into the catheter and support member from the proximal end of the catheter, e.g., see FIG. 2.

Reactants disposed in a solid phase may be particles that include one or more of the reactants. Particles may be disposed in the support member, catheter, or both prior to positioning the support member at the implant site. For example, particles may be disposed in the support member at the time of fabrication of the delivery system. Also, particles may be suspended in a fluid which can be injected into the catheter and support member. The reactant in the particles may be capable of being dissolved by the fluid so that the reaction may occur in the fluid phase.

Alternatively, the support member may include a coating on at least a portion of an interior surface of the catheter, the support member, or both. The coating may include at least one of the reactants. In one embodiment, the coating may be composed completely or substantially of one or more of the reactants. In another embodiment, the coating may include a mixture of one or more reactants and nonreactive material. A coating may be applied to an interior surface of the balloon using any commonly known method such as spraying or dipping. Coating material may be applied as a mixture of a solvent, one or more reactants, and nonreactive material. All or substantially all of the solvent may then be removed to form the coating.

Furthermore, reactants may be allowed to react in several ways. In one embodiment, a fluid including the first and second reactants may be disposed into the delivery system. The fluid may include the first and the second reactants. Alternatively, the fluid may include the first reactant. Another fluid including the second reactant may be disposed at the same time or after the fluid including the first reactant to allow the reaction of the reactants.

In another embodiment, particles including the first reactant may be disposed within the support member, catheter, or both. A fluid including the second reactant may be disposed into the delivery system to react with the first reactant. At least a portion of the first reactant may be dissolved by the fluid and react with the second reactant in the fluid phase. In some embodiments, at least a portion of the second reactant may diffuse into the particles and react with the first reactant. In an additional embodiment, the injected fluid may have suspended particles that include the second reactant for reacting with the first reactant.

In other embodiments, the catheter, support member, or both may contain particles including both the first and second reactants. Individual particles may have one or both of the reactants. The reactants may react upon exposure of the particles to a fluid injected into the catheter and support member.

In further embodiments, particles with the first reactant suspended in a fluid may be injected into a catheter and support member. Particles with the second reactant suspended in a fluid may then be injected to initiate the reaction.

In an additional embodiment, a fluid including the second reactant may be disposed within the delivery system to react with the first reactant included in a coating. The coating may be above at least a portion of an interior surface of the support member, an interior surface of a catheter in fluid communication with the support member, or both. The first reactant in the coating may be dissolved by the fluid so that first reactant can react with the second reactant in the fluid phase.

Additionally, a coating may include the first reactant and the second reactant. The reactants may react upon exposure of the coating to a fluid disposed into the delivery system.

In addition, the reaction may be initiated at selected times during the delivery. Embodiments may include positioning the mounted stent with the delivery system at an implant site before, during, and/or after allowing the first reactant and the second reactant to react.

In some embodiments, the method may further include mixing a fluid within the delivery system including the first reactant and second reactant to facilitate the reaction. A mixing device may be within or coupled to the support member, catheter, or both. Alternatively, the flow of fluid in the delivery system may be sufficient to mix the fluid to allow the reaction.

Additionally, the increase in temperature can be controlled by, for example, selecting reactants with a particular heat of reaction and the amount of reactants disposed within the delivery system. A reaction with a higher heat of reaction and a greater amount of reactants in the delivery system tends to result in a higher increase in temperature.

Also, it may be desirable to control the duration of heating of the stent. In one embodiment, the duration may be controlled by increasing or decreasing the amount of reactants in the delivery system. For example, the amount of coating material on the interior surface of the balloon or catheter may be altered to control the amount and duration of the heating of the stent. The duration and amount of heat may also be controlled by altering the amount nonreactive material in the coating. For example, increasing the amount of nonreactive material may increase the duration of heating as well as decrease the rate of heating of the stent.

It may be desirable to have a relatively high rate of heating and/or heat of reaction so that the stent can be heated relatively quickly to increase the flexibility during the expansion process. In one embodiment, a balloon may be partially expanded prior to disposing a fluid into the balloon which initiates the reaction. The stent may be allowed to increase in temperature from the heat of the reaction prior to further expansion. After a period of time, during which the temperature of the stent in increased, the stent can be further expanded.

In addition, the duration of a reaction may be controlled by limiting the amount of reactant in a fluid, a coating, or particle. The reaction will terminate once one of the reactants is consumed.

Figure 5:
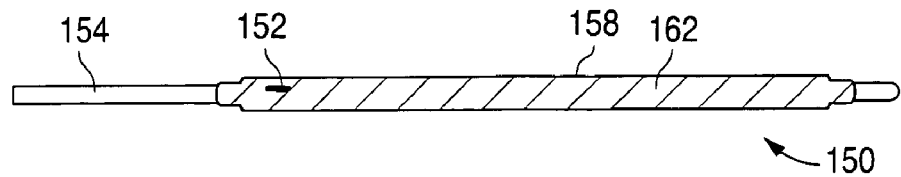
FIG. 5 depicts a portion of an axial cross-section of a delivery system with a balloon having a coating on an interior surface.

FIG. 5 depicts a portion of an axial cross-section of a delivery system 150 that includes a catheter 154 in fluid communication with an expandable member or balloon 158 with a lumen port 152. Balloon 158 is shown in a crimped or deflated state. A stent (not shown) can be mounted on balloon 158 as illustrated in FIGS. 2-3. An interior surface of balloon 158 has a coating 162 that includes a first reactant.

Figure 6:
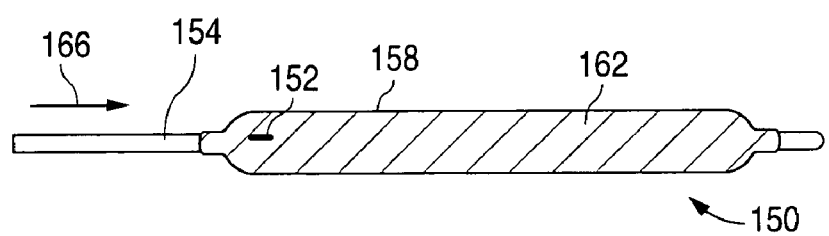
FIG. 6 depicts the delivery system of FIG. 5 with the balloon inflated.
Figure 7:
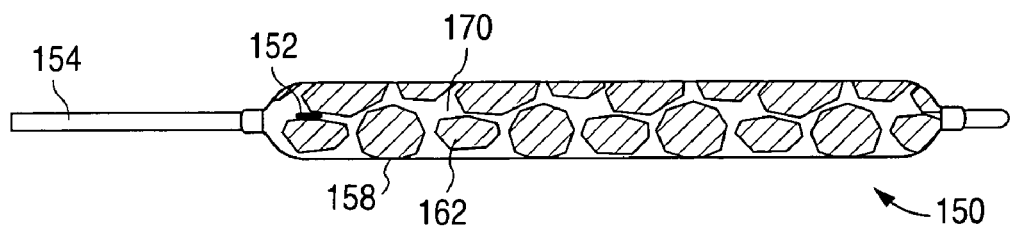
FIG. 7 depicts the delivery system of FIG. 5 with the balloon fully inflated.

FIG. 6 depicts delivery system 150 as balloon 158 is inflated. A fluid containing a second reactant is injected into and flows through catheter 154 as shown by an arrow 166. Fluid fills balloon 158 causing balloon 158 to inflate. The first reactant in the coating and the second reactant in the fluid react as fluid enters balloon 158 and inflates the balloon. A stent (not shown) mounted on the balloon is heated by the heat generated by the exothermic reaction. FIG. 7 depicts delivery system 150 with balloon 158 fully inflated. Coating 162 has been partially consumed by the reaction as shown by depleted portions 170.

Figure 8:
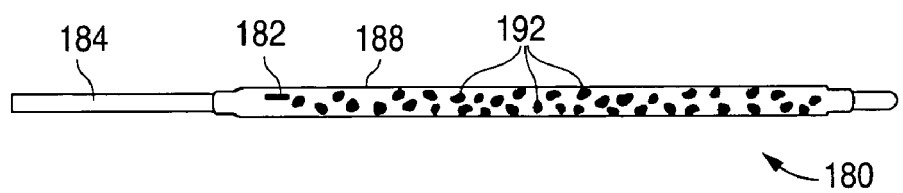
FIG. 8 depicts a portion of an axial cross-section of a delivery system with a balloon having particles disposed within.

FIG. 8 depicts a portion of an axial cross-section of a delivery system 180 that includes a catheter 184 in fluid communication with an expandable member or balloon 188 with a lumen port 182. As in FIG. 5, balloon 158 is shown in a crimped or deflated state. Particles 162 including a first reactant are disposed within balloon 158.

Figure 9:
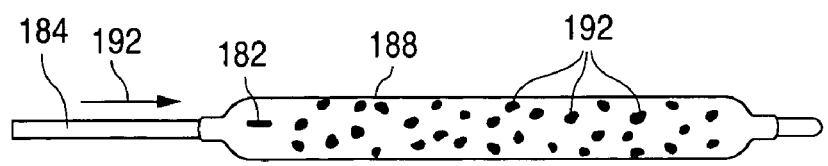
FIG. 9 depicts the delivery system of FIG. 8 with the balloon inflated.

FIG. 9 depicts delivery system 180 as balloon 188 is inflated. A fluid flows through catheter 184 as shown by an arrow 192. Fluid fills balloon 188 causing balloon 188 to inflate. The first reactant in the particles and the second reactant in the fluid react as fluid enters balloon 188 and inflates the balloon. As described before, a stent (not shown) mounted on the balloon is heated by the heat generated by the exothermic reaction.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of delivering a stent mounted on a support member of a delivery system, comprising:
    expanding a balloon expandable stent crimped tightly over a balloon on the support member by expanding the balloon, wherein the stent comprises a scaffolding made of a biodegradable polymer with a glass transition temperature greater than body temperature,
    wherein a solid coating including a first reactant is on at least a portion of an interior surface of the balloon;
    disposing a fluid including a second reactant within the balloon having the solid coating to react with the first reactant included in the solid coating;
    allowing the first reactant and the second reactant to react within the balloon, wherein the first and the second reactants react exothermically; and
    allowing heat generated from the exothermic reaction to increase a temperature of the balloon expandable stent over the balloon during or after the expansion by the balloon, wherein the increase in temperature increases the flexibility of the stent scaffolding such that formation of cracks in the stent scaffolding upon its expansion is reduced or eliminated.

2. The method of claim 1, wherein the first and second reactants react, before, during, and/or after expansion of the stent.

3. The method of claim 1, further comprising allowing the stent to cool after expansion of the stent.

4. The method of claim 1, wherein the heat from the reaction increases a temperature of the stent at or above a glass transition temperature of the biodegradable polymer.

5. The method of claim 1, further comprising disposing a catalyst in the delivery system to facilitate the reaction.

6. The method of claim 1, wherein the biodegradable polymer is poly(L-lactide).

7. The method of claim 1, wherein first reactant in the coating is dissolved by the fluid so that first reactant can react with the second reactant in the fluid phase.

8. A method of delivering a stent mounted on a support member of a delivery system, comprising:
   expanding a balloon expandable stent crimped tightly over a balloon on the support member by expanding the balloon, wherein the stent comprises a scaffolding made of a biodegradable polymer with a glass transition temperature greater than body temperature,
   wherein a solid coating including a first reactant and a second reactant is on at least a portion of an interior surface of the balloon;
   disposing a fluid into the balloon having the solid coating;
   allowing the first reactant and the second reactant to react within the balloon upon exposure of the coating to the fluid, wherein the first and the second reactants react exothermically; and
   allowing heat generated from the exothermic reaction to increase a temperature of the balloon expandable stent over the balloon during or after the expansion by the balloon, wherein the increase in temperature increases the flexibility of the stent scaffolding such that formation of cracks in the stent scaffolding upon its expansion is reduced or eliminated.

9. A method of delivering a stent mounted on a catheter of a delivery system, comprising:
   expanding a balloon expandable stent crimped tightly over a balloon on the catheter by expanding the balloon, wherein the stent comprises a scaffolding made of a biodegradable polymer with a glass transition temperature greater than body temperature,
   wherein a solid coating including a first reactant is on at least a portion of an interior surface of the catheter in fluid communication with the balloon;
   disposing a fluid including a second reactant into the delivery system to react with the first reactant included in the solid coating;
   allowing the first reactant and the second reactant to react, wherein the first and the second reactants react exothermically; and
   allowing heat generated from the exothermic reaction to increase a temperature of the balloon expandable stent over the balloon during or after the expansion by the balloon, wherein the increase in temperature increases the flexibility of the stent scaffolding such that formation of cracks in the stent scaffolding upon its expansion is reduced or eliminated.

\* \* \* \* \*